United States Patent
Arena et al.

(10) Patent No.: US 7,384,743 B2
(45) Date of Patent: Jun. 10, 2008

(54) BRCA1/BCRA2 SCREENING PANEL

(75) Inventors: Jose F. Arena, Rockville, MD (US); Lisa Baumbach-Reardon, Plantation, FL (US); Luis Gayol, Miami, FL (US); Mary Ellen Ahearn, Miami Shores, FL (US)

(73) Assignee: University of Miami, Miami, FL (US)

( * ) Notice: Subject to any disclaimer, the term of this patent is extended or adjusted under 35 U.S.C. 154(b) by 462 days.

(21) Appl. No.: 10/687,328

(22) Filed: Oct. 16, 2003

(65) Prior Publication Data

US 2004/0115717 A1 Jun. 17, 2004

Related U.S. Application Data

(60) Provisional application No. 60/418,910, filed on Oct. 16, 2002.

(51) Int. Cl.
*C12Q 1/68* (2006.01)
*C12P 19/34* (2006.01)

(52) U.S. Cl. .......................................... 435/6; 435/91.2

(58) Field of Classification Search ..................... None
See application file for complete search history.

(56) References Cited

U.S. PATENT DOCUMENTS 5,538,848 A * 7/1996 Livak et al. .................... 435/6

OTHER PUBLICATIONS

Panguluri et al. (Human Genetics (1999) 105:28-31.*
Judkins et al. (Mutation Research, 2005, vol. 573, pp. 168-179).*
Phelan et al. Journal of Medical Genetics, 2005, vol. 42, pp. 138-146*
Baumbach et al., "Cancer Genetics and Genomics," Abstract, 2003 American Society of Human Genetics BRCA Abstract.
Olopade et al., "Breast Cancer Genetics in African Americans," Cancer Supplement, 97: 236-245, 2003.
Kanaan et al., "Inherited BRCA2 mutations in African Americans with breast and/or ovarian cancer: a study of familial and early onset cases," Hum Genet, 113: 452-460, 2003.
Gao et al., "Prevalence of BRCA1 and BRCA2 mutations among clinic-based African American families with breast cancer," Hum Genet, 107: 186-191, 2000.
Gao et al., "Protein truncating BRCA1 and BRCA2 mutations in African women with pre-menopausal breast cancer," Hum Genet 107: 192-194, 2000.
Panguluri et al., "BRCA1 mutations in African Americans," Hum Genet, 105: 28-31, 1999.
Newman et al., "Frequency of Breast Cancer Attributable to BRCA1 in a Population-Bases Series of American Women," JAMA, 279: 915-921, 1998.
Scholl et al., "BRCA1 IVS16+6T→C Is a Deleterious Mutation That Creates an Aberrant Transcript by Activating a Cryptic Splice Donor Site," American Journal of Medical Genetics, 85: 113-116, 1999.

* cited by examiner

*Primary Examiner*—Juliet C. Switzer
(74) *Attorney, Agent, or Firm*—Akerman Senterfitt; Gregory A. Nelson; Amy A. Dobbelaere

(57) ABSTRACT

A method for analyzing a biological sample is performed by analyzing a biological sample for the presence of one or more mutations or polymorphisms in the BCRA1 and/or BCRA2 genes.

9 Claims, No Drawings

BRCA1/BCRA2 SCREENING PANEL

CROSS-REFERENCE TO RELATED APPLICATIONS

The present application claims the priority of U.S. provisional patent application Ser. No. 60/418,910 filed Oct. 16, 2002.

STATEMENT AS TO FEDERALLY SPONSORED RESEARCH

Not applicable.

FIELD OF THE INVENTION

The invention relates generally to the fields of molecular biology, medical diagnostics, and genomics. More particularly, the invention relates to the discovery of novel BRCA1/BCRA2 mutations or polymorphisms associated with breast cancer and with the development of a BRCA1/BCRA2 mutation screening panel.

BACKGROUND

African-American (AA) women under 50 years of age have the highest rate of new cases of breast cancer in the nation and tend to present at an earlier age with larger tumors and more advanced stage disease. This excess in breast cancer incidence among young AA women may be due to increased exposure to known risk factors, and/or a decreased exposure to protective factors, or due to genetic factors. Extensive studies designed to detect a possible molecular basis for this difference have not been reported.

A commercially available service for assessing a woman's risk of acquiring breast cancer involves detecting mutations in two genes—BRCA1 and BRCA2. This service is relatively expensive as it involves complete sequencing of these genes. Other methods for screening for BRCA1 and BRCA2 mutations include single stranded conformational polymorphism (SSCP) analysis and selected DNA sequencing of gene variants, or DHPLC and DNA sequencing of gene variants. These are labor-intensive, and would therefore likely be expensive if commercially implemented. Accordingly what is needed is a compilation of BRCA1 and BRCA2 mutations that could be used for screening for specific mutations/variants in subjects, particularly AA women.

SUMMARY

The invention relates to the development of an efficient screening panel for BRCA1 and BRCA2 mutations/variants that is especially useful for evaluating the risk of breast cancer development in AA women. This panel is based on the identification of several different mutations/polymorphisms in the BRCA1 and BRCA2 genes. A number of different screening strategies can be used to detect these mutations/polymorphisms including for example, direct sequencing of polymerase chain reaction (PCR) amplification products, real time PCR, and a combination of PCR and multiplex SSCP analysis. Site-directed mutagenesis has been used to synthesize mutation-positive controls for several of the mutations/polymorphisms within the panel. By determining the presence of these BRCA1/BRCA2 mutations/variants in a biological sample taken from a test subject, that subject predisposition to developing breast cancer can be assessed without the necessity of sequencing the entire BRCA1 and BRCA2 genes.

Accordingly the invention features a method for analyzing a biological sample that includes the steps of: (a) obtaining the biological sample from a subject; and(b) analyzing the sample for the presence of a genetic polymorphism or mutation that includes a cytosine to thymine transition at position 4959 in the BRCA1 gene (4959C>T), an adenine to guanine transition at position 5217 in the BRCA1 gene (5217G>A), an adenine to guanine transition at position 1503 in the BRCA2 gene (1503A>G), an adenine to cytosine transition at position 5996 in the BRCA2 gene (5996A>C), and/or an adenine to cytosine transition at position 8688 in the BRCA2 gene (8688A>C).

The method can further include a step of analyzing the sample for the presence of additional genetic polymorphisms or mutations such as 676C>A, 943ins10,1010G>A, 062A>G,1183A>G, 1186A>G, 1256T>G, 1625del5, 1680G>A, 1742insG, 1832del5, 2577A>G, 3450del5, 3537A>G, 3667A>G, 3719G>C, 3875del4, 3883insA, 3888delG, 3987A>T, 4009C>T, 4160delAG, 4476G>A, 4810T>C, 4932T>C, 5273G>T, 5296del4, 5472G>T, 5501G>T, IVS13+1G>A, IVS16+6T>C, IVS16–20A>G, IVS18+85delT, IVS22+5G>T, IVS22+8T>A, IVS22+8T>C, IVS22+68T>C, 3'UTR+36 C>G from BCRA1, and 203G>A, 459T>G, 1342C>A, 1536del4, 2016T>C, 2816insA, 3014T>C, 3034del4, 3188A>T, 4791G>A, 5932G>A, 6575A>G, 6696delTC, 6741C>G, 7245G>C, 7378C>A, 7470A>G, 7697T>C, 7795delCT, and 9862G>C from BCRA2.

In the method, the biological sample can be a blood or tissue sample, and the step of analyzing the sample for the presence of the genetic polymorphism or mutation can include performing a polymerase chain reaction (PCR) step, e.g., to amplify a nucleic acid having the genetic polymorphism or mutation. The step of analyzing the sample for the presence of the genetic polymorphism or mutation can further include a step of determining the nucleotide sequence of the nucleic acid having the genetic polymorphism or mutation, and/or a step of analyzing the nucleic acid by SSCP analysis.

Unless otherwise defined, all technical terms used herein have the same meaning as commonly understood by one of ordinary skill in the art to which this invention belongs. Definitions of molecular biology terms can be found, for example, in Rieger et al. (1991) Glossary of Genetics: Classical and Molecular, 5th edition, Springer-Verlag: New York; and Lewin, (1994) Genes V, Oxford University Press: New York.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

DETAILED DESCRIPTION

The invention provides compositions and methods relating to a screening panel for BRCA1 and BRCA2 mutations/polymorphisms that can be used to evaluate the risk of breast cancer development in subjects, particularly AA women. The screening panel includes a compilation of several known and several previously uncharacterized mutations/ polymorphisms in the BRCA1 and BRCA2 genes. To assess a subject's risk of developing breast cancer, a biological sample obtained from the subject is analyzed for the presence of one or more of these mutations or polymorphisms. For example, the sample can be screened against between 1-30 or more different mutations/polymorphisms using positive controls (e.g., nucleic acid molecules known to harbor the mutations/polymorphisms being screened for) and negative controls (e.g., nucleic acid molecules known not to harbor the mutations/polymorphisms being screened for). The presence of one or more of these mutations or polymorphisms indicates that the subject is at higher risk for developing breast cancer than others in the general population. The invention is advantageous over the method of sequencing the entire BRCA1 and BRCA2 genes and looking for mutations anywhere in the nucleotide sequences because it focuses only on those mutations/polymorphisms associated with breast cancer development. By focusing on these particular mutations/polymorphisms, the panel allows for an easier way to perform a more efficient and accurate breast cancer risk determination.

The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al. (2001) Cold Spring Harbor Laboratory Press, Cold Spring Harbor, N.Y.; and Current Protocols in Molecular Biology, ed. Ausubel et al. (1992) Greene Publishing and Wiley-Interscience, New York (with periodic updates). Various techniques using polymerase chain reaction (PCR) are described, e.g., in Innis et al. (1990) PCR Protocols: A Guide to Methods and Applications, Academic Press: San Diego. PCR-primer pairs can be derived from known sequences by known techniques such as using computer programs intended for that purpose (e.g., Primer, Version 0.5, 1991, Whitehead Institute for Biomedical Research, Cambridge, Mass.). Techniques relating to PCR-mediated mutagenesis are described in Higuchi, R., Recombinant PCR. *In: PCR Protocols. A Guide to Methods and Applications*. pp. 177-183. Academic Press, San Diego, Calif., 1990. Methods for chemical synthesis of nucleic acids are discussed, for example, in Beaucage and Carruthers (1981) Tetra. Letts. 22:1859-1862 and Matteucci et al. (1981) J. Am. Chem. Soc. 103:3185. Chemical synthesis of nucleic acids can be performed, for example, on commercial automated oligonucleotide synthesizers.

BRCA1/BRCA2 Mutations and Polymorphisms

The invention involves screening a biological sample obtained from a women for the presence of one or more different BRCA1 and BRCA2 gene mutations/polymorphisms. The nucleotide sequences for the native (non-mutant; non-polymorphic) BRCA1 and BRCA2 genes and their corresponding amino acid sequences are known. See U.S. Pat. No. 5,654,155; Tavtigian, S. V. et al, (1996), The complete BRCA2 gene and mutations in chromosomes 13q-linked Kindreds, Nature Genetics 12, pp. 333-337. Examples of known and newly identified BRCA1 and BRCA2 gene mutations/polymorphisms are shown in Tables 1 and 2 below. Any one or any combination of these mutations/polymorphisms can be screened for. For example, a panel of BRCA1 and BRCA2 gene mutations/polymorphisms might include 2, 3, 4, 5, 6, 7, 8, 9, 10, 11, 12, 13, 14, 15, 16, 17, 18, 19, 20, 21, 22, 23, 24, 25, 26, 27, 28, 29, 30, or more of the mutations/polymorphisms listed in Tables 1 and 2. For thoroughness, it is preferred that all or almost all of the different BRCA1 and BRCA2 gene mutations/polymorphisms are examined in any one analysis.

Analyzing a Biological Sample for the Presence of BRCA1 and BRCA2 Gene Mutations/Polymorphisms The invention provides a method for assessing selected genetic factors which contribute to the risk of a subject (e.g., an AA woman) for developing breast cancer. The method is performed by obtaining a biological sample (e.g., blood or saliva) from the subject, and analyzing DNA within the sample for the presence of one or more of the above-described BRCA1 and BRCA2 gene mutations/polymorphisms. A number of methods for determining the presence of a particular nucleotide sequence in a sample are known. See, e.g., Ausubel et al., supra. Any of these might be used in the methods of the invention. For example, PCR can be used to amplify predetermined portions of BRCA1 or BRCA2 genomic DNA. The nucleotide sequence of the amplified portions can then be determined using conventional techniques, e.g., sequencing. Other PCR-based methods (e.g., using primers specific for only the mutated/polymorphic DNA; or real time PCR) or SSCP might be used. See, e.g., Fox and Parks (2001) Clinical Chemistry 47:990-1000, "Emerging Homogeneous DNA-based Technologies in the Clinical Laboratory" and Hayashi, K. (1991) PCR Methods and Applications 1:34-38. "PCR-SSCP: A Simple and sensitive method for detection of mutations in the genomic DNA" The biological sample might also be analyzed by contacting the sample with nucleic acid probes that hybridize preferentially to nucleotide sequences that harbor the mutation/polymorphism, e.g., by Southern blotting or perhaps fluorescence in situ hybridization techniques. The presence of certain BRCA1 and BRCA2 mutations/polymorphisms in a sample might also be determined indirectly, by, for example, analyzing (1) mRNA (or cDNA) for the presence of transcribed sequences that correspond to the mutations shown in Tables 1 and 2, or (2) polypeptide products of the mutated/polymorphic BRCA1 and BRCA2 genes.

In each of the foregoing methods, the use of positive and negative controls is preferred to ensure the accuracy of the analysis. Positive controls can take the form of nucleic acid molecules or proteins that have the same sequences that correspond to the nucleic acids of the mutant/polymorphic BRCA1 and BRCA2 genes or proteins encoded by such genes. Negative controls can take the form of nucleic acid molecules or proteins that have the same sequences that correspond to the nucleic acids of the wild-type (non-mutant; non-polymorphic) BRCA1 and BRCA2 genes or proteins encoded by such genes.

EXAMPLES

The present invention is further illustrated by the following specific examples. The examples are provided for illustration only and are not to be construed as limiting the scope or content of the invention in any way.

Example 1

BCRA1 Mutations/Polymorphisms

Table 1 lists several mutations/polymorphisms in the BRCA1 gene identified in AA women. Nucleotide changes shown as X>Y mean that nucleotide X has been replaced with nucleotide (Y). ins=nucleotide insertion; del=nucleotide deletion (where followed by a number N, this means N nucleotides have been inserted/deleted; where followed by one or more A, G, T, or Cs, this means that those nucleotides have been added or inserted); IVS=Intervening sequences or introns; IVS16+6=the sixth nucleotide after the splice site in the sixteenth intron, IVS16-20=the variant is located in the sixteenth intron, 20 nucleotides before the splice site for exon 17. UTR=untranslated region. Amino acid mutants are expressed herein as $X_1PX_2$, where P is a number corresponding to the position of the mutated amino acid in the native BRCA1 or BRCA2 protein, $X_1$ is the letter abbreviation of the amino acid that was replaced, and $X_2$ is the letter abbreviation of the replacement amino acid. For example, S186Y represents a mutant form of the native human BCRA1 protein that has the serine residue that naturally occurs at position 186 in native BRCA1 replaced with a tyrosine residue.

TABLE 1

| BCRA-1 Nucleotide | Mutation/Polymorphism | Amino Acid |
|---|---|---|
| 676 | C > A | S186Y |
| 943 | ins10 | |
| 1010 | G > A | M297I |
| 1062 | A > G | |
| 1183 | A > G | K355R |
| 1186 | A > G | Q356R |
| 1256 | T > G | I379M |
| 1625 | del5 | |
| 1680 | G > A | A521T |
| 1742 | insG | |
| 1832 | del5 | |
| 2577 | A > G | K820E |
| 3450 | del4 | |
| 3537 | A > G | S1140G |
| 3667 | A > G | K1183R |
| 3719 | G > C | Q1200H |
| 3875 | del4 | |
| 3883 | insA | |
| 3888 | delG | |
| 3987 | A > T | K1290X |
| 4009 | C > T | S1297F |
| 4160 | delAG | |
| 4810 | T > C | L1564P |
| 4932 | T > C | L1605L |
| 4959 | C > T | P1614S |
| 5217 | A > G | T1700A |
| 5273 | G > T | W1718C |
| 5296 | del4 | |
| 5472 | G > T | Q1785H |
| 5501 | G > T | E1794D |
| IVS13 + 1 | G > A | |
| IVS16 + 6 | T > C | |
| IVS16 − 20 | A > G | |
| IVS18 + 85 | delT | |
| IVS22 + 5 | G > T | |
| IVS22 + 8 | T > A | |
| IVS22 + 8 | T > C | |
| IVS22 + 68 | T > C | |
| 3'UTR + 36 | C > G | |

Example 2

BCRA2 Mutations/Polymorphisms

Table lists several mutations/polymorphisms in the BRCA2 gene identified in AA women. Abbreviations are the same as in Table 1.

TABLE 2

| BCRA-2 Nucleotide | Mutation/Polymorphism | Amino Acid |
|---|---|---|
| 203 | G > A | |
| 459 | T > G | |
| 1342 | C > A | H372N |
| 1503 | A > G | |
| 1536 | del4 | |
| 2016 | T > C | |
| 2816 | insA | |
| 3014 | T > C | L929S |
| 3034 | del4 | |
| 3188 | A > T | N987I |
| 4791 | G > A | |
| 5932 | G > A | H2116R |
| 5996 | A > C | D1923A |
| 6575 | A > G | H2116R |
| 6696 | delTC | |
| 6741 | C > G | |
| 7245 | G > C | K2339N |
| 7378 | C > A | Q2384K |
| 7470 | A > G | S2414S |
| 7697 | T > C | I2490T |
| 7795 | delCT | |
| 8688 | A > C | |
| 9862 | G > C | G3212R |

Example 3

Frequency of BRCA1/2 Mutation/Variants Found in African-American Breast Cancer Patients and Controls BRCA1 and BRCA2 variants listed in Table 3 were analyzed for their overall frequency in two ways. First, BIC (the Breast Cancer Information Source), which is a publicly-accessible database for voluntary deposition of BRCA1/BRCA2 mutations and genetic variants was specifically searched for the variant listed. If found, the number of times it was deposited in BIC was recorded, as well as information regarding African-American ancestry, and information regarding type of mutation. Non-deleterious (non-protein truncating) variants were then checked for their frequency in either African-American or Caucasian control (non-breast cancer) samples (CH=chromosomes), with the standard test being 100 chromosomes (50 individuals) analyzed.

TABLE 3

| Mutation/Variant | BIC ENTRY | # of fam | AA Contr | Wh Contr |
|---|---|---|---|---|
| BRCA1 | | | | |
| S186Y (676C > A) | 10/3AA M UV | 1 | 0%(100Ch) | |
| *943ins10* | 8/2AA F F | 3 | N/A | |
| S1140G (3537A > G) | 27/3AA M UV | 3 | 4%(100Ch) | 0% (46Ch) |
| *3875del4* | 73/1AA F F | 1 | N/A | |
| *3888delG* | 0/0 | 1 | N/A | |
| *4160delAG* | 3/? F F | 1 | N/A | |
| P1614S (4959C > T) | 0/0 | 1 | 0%/(100Ch) | |
| T1700A (5217A > G) | 0/0 | 1 | 0%(100Ch) | |
| *W1718C(5273G>T)* | 1/? M UV | 1 | 0%(100Ch) | |
| *IVS13+1 G>A* | 5/2AA S S | 1 | N/A | |
| *IVS16+6 T>C* | 5/2 S S | 1 | 0%/(100Ch) | |
| IVS16 − 20 A > G | 8/2AA UV UV | 1 | 1%(100Ch) | |
| IVS18 + 85delT | 0/0 | 3 | 9%(100Ch) | |
| IVS22 + 8 T > C | 12/1AA P P | 1 | 1%(100Ch) | 0% (50Ch) |
| IVS22 + 67 T > C | 0/0 | 1 | 5%(140Ch) | 0% (50Ch) |
| 3'UTR + 36 C > G | 6/0 P | 2 | 6%(140Ch) | 0% |

TABLE 3-continued

| Mutation/Variant | BIC ENTRY | # of fam | AA Contr | Wh Contr |
|---|---|---|---|---|
| BRCA2 | | | | (50Ch) |
| 203G > A | 10/0 UTR P | 5 | No studied | |
| T77T (459T > G) | 0/0 | 1 | 0%(100Ch) | |
| H372N (1342C > A) | 9/0AA M P | 7 | 7%(100Ch) | |
| E425E (1503A > G) | 0/0 | 1 | 2%(100Ch) | |
| D596D (2016T > C) | 1/? AA P P | 1 | 5%(100Ch) | |
| L1521L (4791G > A) | 2/1AA P P | 5 | 3%(100Ch) | |
| D1902N (5932G > A) | 27/9AA M UV | 2 | 3%(100Ch) | |
| D1923A (5996A > C) | 0/0 | 1 | 0%(100Ch) | |
| H2116R (6575A > G) | 36/7AA M UV | 2 | 0%(100Ch) | |
| V2171V (6741C > G) | 1/1AA P P | 5 | 3%(100Ch) | |
| S2414S (7470A > G) | 10/0 Syn P | 2 | 45%(100Ch) | |
| I2490T (7697T > C) | 88/1AA M UV | 1 | 0%(100Ch) | |
| V2820V (8688A > C) | 0/0 | 1 | 3%(100Ch) | |

Notes to table:
BIG Entry as of April 2003: times reported/#AA with the mut/variant reported, mutation type, mutation effect. (M = missense variant, UV = variant of unknown clinical significance, FF = frameshift mutation, SS = splicing mutation; PP or P = presumed polymorphism, UTR = untranslated region).
# of fam: Number of families in which a specific mutation/variant was found in the laboratory at University of Miami;
AA Contr: African-American controls.
Wh Contr: Caucasian controls. Deleterious mutations are written in bold and italic.

Example 4

BRCA1 and BRCA2 Linkage Disequilibrium Found in African-American Breast Cancer Families

BCRA1

IVS22+8 T>C linked with 3'UTR+36 C>G. In one family, this linkage was found in 3 unaffected members (2 female, one male). In another family, this was found in the proband in conjunction with 3 other BRCA1 missense mutations and one BRCA2 polymorphism; no other members were studied. The frequency of these linked polymorphisms is 1% of African-American controls studied and 0% of Caucasian controls.

IVS22+68 T>C linked with 3'UTR+36 C>G. Found in one family in all affected females as well as in two unaffected females (below the age of onset for breast cancer) and two males. These polymorphisms cosegregate in this family with the W1218C mutation in Exon 19. This segregation analysis strongly suggests that the haplotype is linked to disease in this family. The frequency of the polymorphisms is 5% in African-American controls and 0% in Caucasian controls.

BRCA2

L1521L (479G>A) linked with V2171V (6741 C>G). These two Exon 11 polymorphisms have been found in 5 breast cancer patients from 5 different, non-related families. The frequency in African-American controls is 3%.

OTHER EMBODIMENTS

While the above specification contains many specifics, these should not be construed as limitations on the scope of the invention, but rather as examples of preferred embodiments thereof. Many other variations are possible. Therefore to apprise the public of the scope of the invention and the embodiments covered by the invention, the following claims are made.

What is claimed is:

1. A method for analyzing a biological sample from an African American woman for the presence of a polymorphism or mutation associated with breast cancer comprising the steps of:
    (a) obtaining the biological sample from an African American subject;
    (b) analyzing the sample for the presence of an adenine to guanine transition at position 5217 in the BRCA1 gene (5217 A>G); and
    (c) detecting the presence of a guanine at position 5217 of the BRCA1 gene.

2. The method of claim 1, wherein the step (b) of analyzing the sample for the presence of an adenine to guanine transition at position 5217 in the BRCA1 gene (5217 A>G) further comprises analyzing the sample for the presence of a cytosine to thymine transition at position 4959 in the BRCA1 gene (4959C>T).

3. The method of claim 1, further comprising analyzing the sample for the presence of a genetic polymorphism or mutation selected from the group consisting of 676C<A, 943ins10, 1010G>A, 062A>G, 1183A>G, 1186A>G, 1256T>G, 1625del5, 1680G>A, 1742insG, 1832del5, 2577A>G, 3450del5, 3537A>G, 3667A>G, 3719G>C, 3875del4, 3883insA, 3888delG, 3987A>T, 4009C>T, 4160delAG, 4476G<A, 4810T<C, 4932T<C, 5273G<T, 5296del4, 5472G<T, 5501G<T, IVS13+1G<A, IVS16+6T<C, IVS16−20A<G, IVS18+85delT, IVS22+5G<T, IVS22+8T<A, IVS22+8T<C, IVS22+68T<C, 3'UTR+36 C<G from BRCA1, and 203G<A, 459T<G, 1342C<A, 1536del4, 2016T<C, 2816insA, 3014T<C, 3034del4, 3188A<T, 4791G<A, 5932G<A, 6575A<G, 6696delTC, 6741C<G, 7245G<C, 7378C<A, 7470A<G, 7697T<C, 7795delCT, and 9862G<C from BCRA2.

4. The method of claim 1, wherein the biological sample is a blood or tissue sample.

5. The method of claim 1, wherein the step (b) of analyzing the sample for the presence of adenine to guanine transition at position 5217 in the BRCA1 gene comprises performing a polymerase chain reaction (PCR) step.

6. The method of claim 5, wherein the PCR amplifies a nucleic acid comprising the adenine to guanine transition at position 5217 in the BRCA1 gene.

7. The method of claim 6, wherein the step (b) of analyzing the sample for the presence of the adenine to guanine transition at position 5217 in the BRCA1 gene further comprises determining the nucleotide sequence of the nucleic acid comprising the adenine to guanine transition at position 5217 in the BRCA1 gene.

8. The method of claim 5, wherein the PCR is real time PCR.

9. The method of claim 6, further comprising analyzing the nucleic acid by single-stranded conformational polymorphism analysis.

* * * * *